US00RE40403E

(19) United States
(12) Reissued Patent
Cho et al.

(10) Patent Number: US RE40,403 E
(45) Date of Reissued Patent: Jun. 24, 2008

(54) METHOD FOR NON-INVASIVE WRINKLE REMOVAL AND SKIN TREATMENT

(75) Inventors: George Cho, Hopkinton, MA (US); Horace W. Furumoto, Wellesley, MA (US); Brian D. Zelickson, Minneapolis, MN (US)

(73) Assignee: Cynosure, Inc., Chelmsford, MA (US)

(21) Appl. No.: 10/176,394

(22) Filed: Jun. 19, 2002

Related U.S. Patent Documents

Reissue of:
(64) Patent No.: 6,077,294
Issued: Jun. 20, 2000
Appl. No.: 09/095,789
Filed: Jun. 11, 1998

(51) Int. Cl.
*A61N 5/67* (2006.01)
*A61B 18/20* (2006.01)

(52) U.S. Cl. ..... 607/89; 607/88; 606/3; 606/9

(58) Field of Classification Search ..... 607/88–93; 606/2, 3, 8–10, 13, 16, 17; 372/30, 53
See application file for complete search history.

(56) References Cited

U.S. PATENT DOCUMENTS

| | | | |
|---|---|---|---|
| 3,766,488 | A | 10/1973 | Kohn |
| 4,176,324 | A | 11/1979 | Aldag et al. |
| 4,292,601 | A | 9/1981 | Aldag et al. |
| 4,829,262 | A | 5/1989 | Furumoto |
| 4,862,886 | A | 9/1989 | Clarke et al. |
| 4,976,709 | A | 12/1990 | Sand |

(Continued)

FOREIGN PATENT DOCUMENTS

WO WO 95/04393 2/1995

OTHER PUBLICATIONS

Dierickx, C.C. et al., "Thermal Relaxation of Port–wine Stain Vessels Probed In Vivo: The Need for 1–10 Millisecond Laser Pulse Treatment," The Journal for Investigative Dermatology, pp. 709–714 (1995).*
Nanni, C.A., and Alster, T.S., "Complications of Carbon Dioxide Laser Resurfacing," *Washington Inst. of Dermatol. Surg.* 24:315–320 (1998).
Reed, J.T. et al., "Treatment of Periorbital Wrinkles," *Washington Inst. of Dermatol. Surg.* 23:643–648 (1997).
Anderson, R.R., et al., "Microvasculature Can Be Selective Damaged Using Dye Lasers: A Basic Theory and Experimental Evidence in Human Skin," *Lasers in Surgery and Medicine,* 1:263–276 (1981).
Anderson, R.R., et al., "Selective Photothermolysis: Precise Microsurgery by Selective Absorption of Pulsed Radiation," *Science,* 220: 524–527, April (1983).
Boiteux, M., et al., "A Transverse Flow Repetitive Dye Laser," *Applied Optics,* 9, 514 (1970).
"Flashlamp Excited Dye Lasers," *Candela Corporation,* 96 South Ave., Natick, Massachusetts 01760, (1979) Commercial Brochure.

(Continued)

*Primary Examiner*—A. Farah
(74) *Attorney, Agent, or Firm*—John M. Garvey; Foley & Lardner LLP

(57) ABSTRACT

A method for the treatment of wrinkles on human skin, by stimulating collagen growth beneath the epidermis layer, comprising the steps of: arranging a pulsed dye laser generator in light communication with a pulsed dye laser delivery device. The pulsed dye laser delivery device is applied against tissue having wrinkles. The pulsed dye laser generator generates a pulsed dye laser light. A pulsed dye laser light from the pulsed dye laser delivery device is directed onto the tissue, to reach hemoglobin in a collagen layer up to about 1.2 mm. beneath the surface of the tissue to effect growth changes therein.

8 Claims, 2 Drawing Sheets

U.S. PATENT DOCUMENTS

| | | | | | |
|---|---|---|---|---|---|
| 4,977,571 | A | | 12/1990 | Furumoto et al. | |
| 5,057,099 | A | | 10/1991 | Rink | |
| 5,066,293 | A | | 11/1991 | Furumoto | |
| 5,092,865 | A | | 3/1992 | Rink | |
| 5,109,387 | A | | 4/1992 | Garden et al. | |
| 5,180,378 | A | | 1/1993 | Kung et al. | |
| 5,287,380 | A | | 2/1994 | Hsia | |
| 5,370,642 | A | | 12/1994 | Keller | |
| 5,387,211 | A | | 2/1995 | Saadatmanesh et al. | |
| 5,405,368 | A | | 4/1995 | Eckhouse | |
| 5,439,954 | A | | 8/1995 | Bush | |
| 5,492,894 | A | | 2/1996 | Bascom et al. | |
| 5,505,727 | A | | 4/1996 | Keller | |
| 5,620,478 | A | | 4/1997 | Eckhouse | |
| 5,624,435 | A | * | 4/1997 | Furumoto et al. | 606/10 |
| 5,626,631 | A | | 5/1997 | Eckhouse | |
| 5,720,772 | A | * | 2/1998 | Eckhouse | 607/88 |
| 5,749,868 | A | | 5/1998 | Furumoto | |
| 5,755,751 | A | | 5/1998 | Eckhouse | |
| 5,807,386 | A | | 9/1998 | Slatkine et al. | |
| 5,810,801 | A | | 9/1998 | Anderson et al. | |
| 5,964,749 | A | | 10/1999 | Eckhouse et al. | |
| 5,983,900 | A | | 11/1999 | Clement et al. | |
| 6,077,294 | A | | 6/2000 | Cho et al. | |
| 6,197,020 | B1 | | 3/2001 | O'Donnell, Jr. | |
| 6,248,103 | B1 | * | 6/2001 | Tannenbaum et al. | 606/9 |

OTHER PUBLICATIONS

Sierra, R., "Flashlamp–Excited Dye Lasers Achieve New Performance Levels," *Laser Focus/Electro–Optics* 2394 (4) : 77–91 (Apr. 1988).

Burlamacchi, P., "A Simple, Reliable Waveguide Dye Laser for Ophthalmological Applications," *Rev. Sci. Instrum.,* 46 (3) :281–3 (Mar. 1975).

M.B. Alora et al., "Comparison of the 595 nm Long–Pulse (1.5ms) and the 595 nm Ultra–Long Pulse (4 ms) Laser in the Treatment of Leg Veins," *American Society for Laser Medicine and Surgery Abstracts,* pg. 32, No date given.

Morton, R.G., "Reliable High average Power High Pulse Energy Dye Laser," *J. Quant. Electron.,* 17:222 Part II, Dec. 1981).

K. Kelly et al., "Nonablative Laser Treatment of Facial Rhytides: United States Phase II Clinical Study," *American Society for Laser Medicine and Surgery Abstracts,* p. 38, No date given.

S. L. Kilmer et al., "Pulse Dye Laser Treatment of Rhytids," *American Society for Laser Medicine and Surgery Abstracts,* p. 44 (Apr. 1997).

J. Dock et al., "Clinical Histologic and Ultrastructural Evaluation of Solar Elastosis Treated With the Pulsed Dye Laser," *American Society for Laser Medicine and Surgery Abstracts,* p. 54 (Apr. 1997).

"A Practical Guide for the PhotoDerm® VL User" (Oct. 1995).

* cited by examiner

METHOD FOR NON-INVASIVE WRINKLE REMOVAL AND SKIN TREATMENT

Matter enclosed in heavy brackets [ ] appears in the original patent but forms no part of this reissue specification; matter printed in italics indicates the additions made by reissue.

BACKGROUND OF THE INVENTION

1. Field of The Invention

The present invention relates to the field of resurfacing skin, or wrinkle removal using laser radiation for treatment of underlying layers of skin.

2. Prior Art

Plastic surgeons, dermatologists and their patients continually search for new and approved methods for treating the effects of an aging skin. Historically, the treatment of facial wrinkles was primarily accomplished with the use of chemical peels or dermabrasion. The use of chemical peels has fallen out of favor, because it is difficult to accurately control and predict the depth of tissue injury after such peels are applied. Deeper chemical peels in particle have an increased risk of hypopigmentation and scarring. Such injury to the top layer of skin, which would be peeled away, would permit new cells to supposedly rejuvenate the skin. A less expensive way of injuring the outer layer of the skin is the utilization of an abrasive wheel, to rough off the skin layer. This method is not well controlled, and is very difficult especially around the eyelids.

Laser skin resurfacing began with a carbon dioxide laser. The carbon dioxide laser energy is absorbed by tissue water causing vaporization of the outer skin layer. Carbon dioxide lasers have been utilized for approximately 3 decades. However it has only been the past few years that these lasers have been arranged to remove only thin tissue layers with minimal heat damage to the surrounding skin. While carbon dioxide lasers may remove about 150 microns of skin, that skin may take a month or more to heal under such a procedure.

Er:YAG lasers have been utilized to ablate even thinner layers of tissue than carbon dioxide layers. However they lack the coagulation characteristics and thus allow more bleeding than a carbon dioxide laser during use.

Non-ablative skin resurfacing, is a methodology which does not take the top layer of skin off, but which shrinks the collagen under the skin, and modifies that collagen, so that the wrinkled skin appears to be fill-in by the collagen modified beneath the skin. This methodology however, has a low efficiency, and a cryogen coolant must be sprayed on to the skin so as to minimize damaging the top or upper layer thereof and also to minimize pain generation. The "fluence" or energy density used is greater than 10 joules per square centimeter and to be more effective this fluence often reaches 30 Joules per square centimeter. This level of energy often causes pain and epidermal damage.

It is an object of the present invention to improve upon the shortcomings of the prior art.

It is yet a further object of the present invention to provide a skin resurfacing laser treatment, which is nonablative, and minimizes any pain to the patient being treated.

It is yet still a further object of the present invention, to provide a new method to stimulate the collagen beneath the skin surface, to improve the surface appearance from beneath that surface of skin of the patient.

BRIEF SUMMARY OF THE INVENTION

The present invention comprises a system and methodology for noninvasive wrinkle removal for the modification of collagen beneath the epidermis. The laser system of the present invention, in a preferred embodiment, utilizes a pulsed dye laser having a deep penetrating wavelength of about 585 nanometers (nm) laser, so as to target hemoglobin of blood in the skin tissue. This particular laser energy is absorbed by the hemoglobin. The heat is generated in the skin area up to about 1 mm in depth and typically uses energy of less than 5 Joules per square cm, having a preferred target spot size of about 10 mm diameter.

The pulsed dye laser apparatus of the present invention includes a handpiece connected by an optical fiber or wave guide, critically, to a pulsed dye laser generator device.

The handpiece focuses, through a plurality of lenses, the pulsed dye laser light from the pulsed dye laser generator, onto the spot of about 10 mm in diameter, so as to stimulate new collagen growth beneath the epidermis without injuring the surrounding structures.

In the preferred embodiment of the present invention, the pulse width has a range of 150 microseconds to about 1500 microseconds with a preferred width of about 450 microseconds. The wavelength of the pulsed dye laser apparatus of the present invention lies in a range of about 570 nanometers to about 650 nanometers, with a preferred wavelength of about 585 nanometers. The present invention provides a preferred fluence of less than 5 Joules per square cm., and preferably 3 Joules per square cm at a 10-millimeter diameter skin treatment spot.

By treating the skin to this low fluence pulsed dye laser light, collagen may be stimulated to regenerate and "fill in" valleys of wrinkles for a younger more clearer skin.

Thus what has been shown is a new method of stimulating modification of the collagen layer at a depth of at least about 1 mm to about 1.2 mm beneath the skin surface, utilizing a low energy level of less than 5 Joules per square cm., in a manner not appreciated by the prior art.

The invention thus comprises a method for the treatment of wrinkles on human skin, by stimulating collagen growth beneath the epidermis layer, comprising the steps of: arranging a pulsed dye laser generator in light communication with a pulsed dye laser delivery device; applying said pulsed dye laser delivery device against tissue having wrinkles; generating a pulsed dye laser light by said pulsed dye laser; and directing said pulsed dye laser light from said pulsed dye laser delivery device onto said tissue, to reach hemoglobin in a collagen layer beneath the surface of said tissue. The method includes the steps of: tuning said pulsed dye laser to deliver a laser light at a wavelength having a range of from about 570 nanometers to about 650 nanometers, and adjusting said range of pulsed dye laser light generated to a wavelength of about 585 nanometers. The pulsed dye laser has a pulse width in a range of from about 150 microseconds to about 1500 microseconds. Preferably the pulsed dye laser has a pulse width of about 450 microseconds. The method included the pulsed dye laser light being directed at the tissue at a target spot diameter of about 10 mm. The method includes maintaining a fluence of the pulsed dye laser light of less than 5 Joules per square cm.

BRIEF DESCRIPTION OF THE DRAWINGS

The objects and advantages of the present invention will become more apparent, when viewed in conjunction with the following drawings, in which.

DESCRIPTION OF THE PREFERRED EMBODIMENTS

Figure 1:
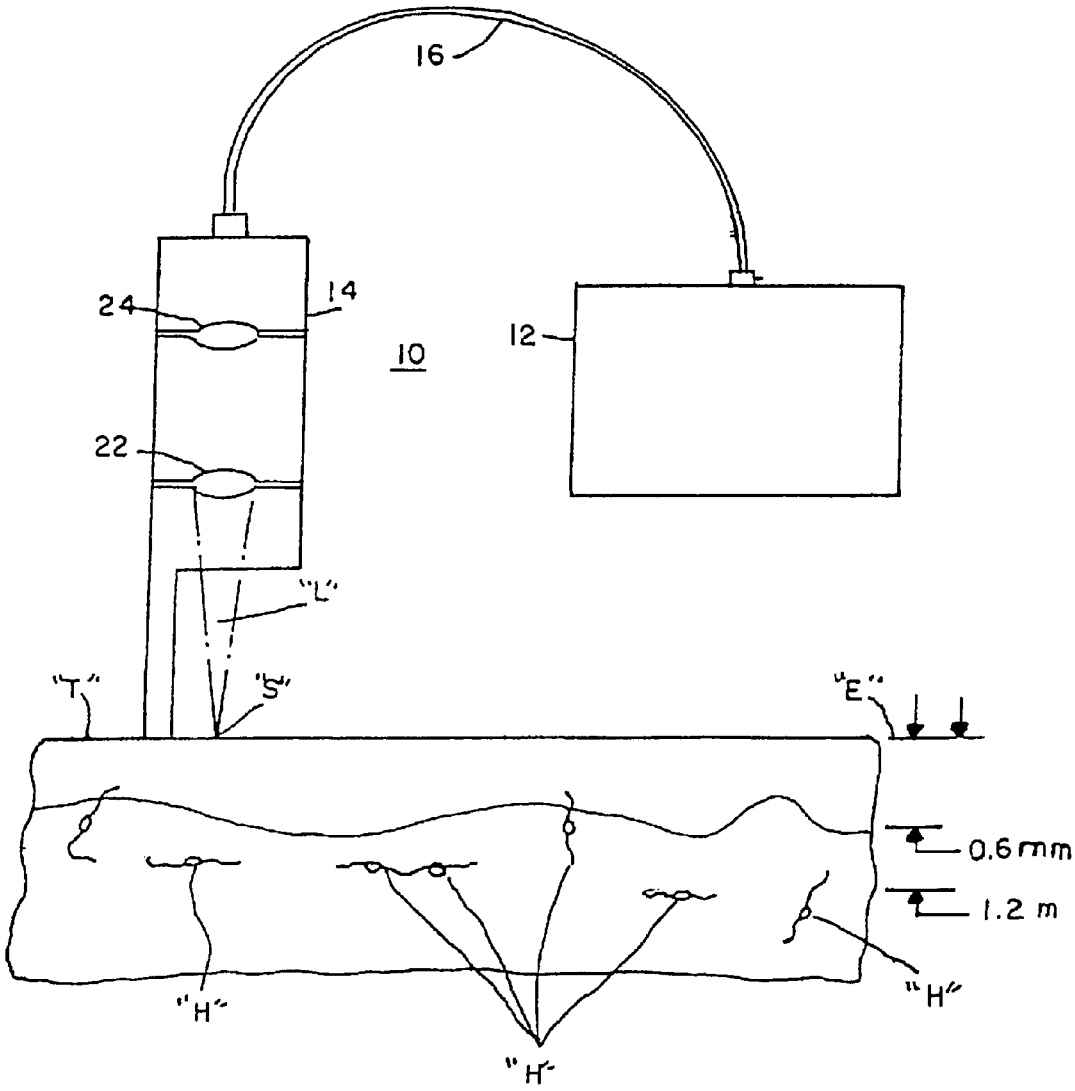
FIG. 1 is a schematic representation of the laser apparatus of the present invention, as it is applied to a layer of skin.
Figure 2:
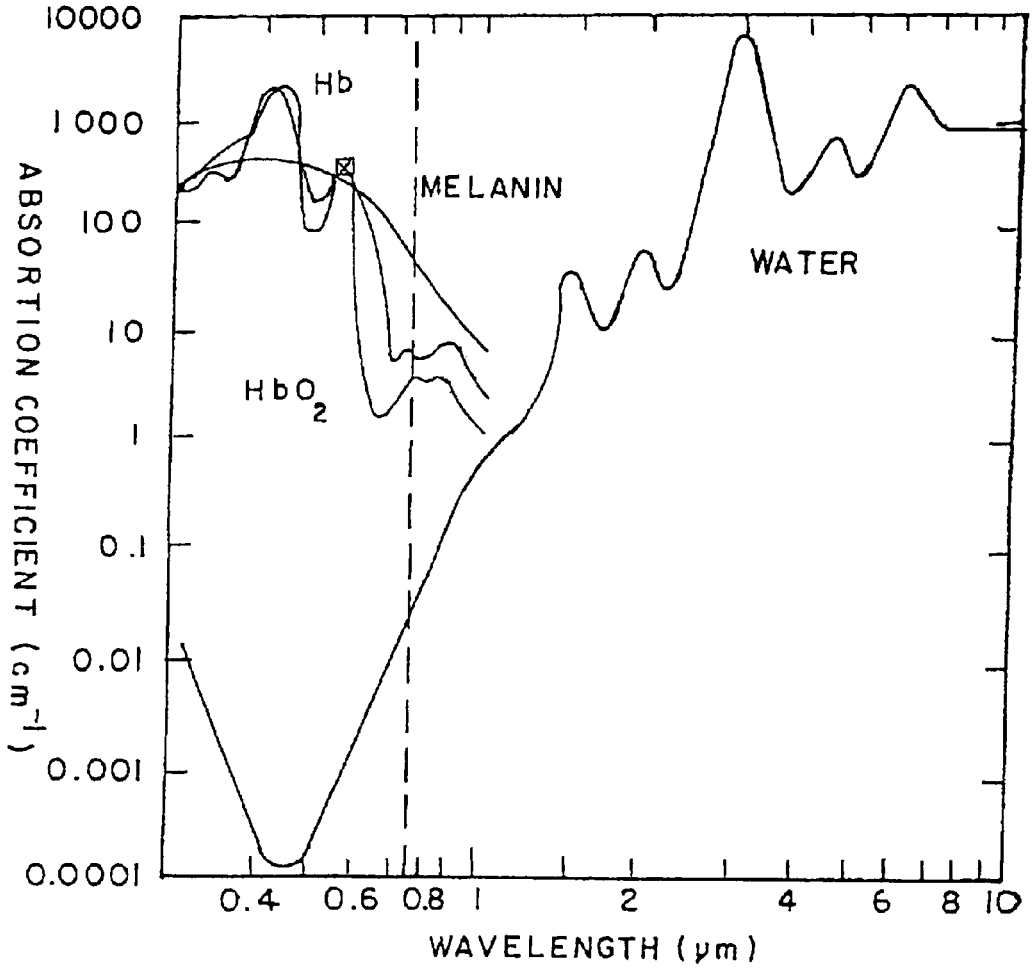
FIG. 2 is a graph showing the absorption characteristics of certain body tissue chromophors versus laser wavelength.

Referring now to the drawings in detail, and particularly to FIG. 1, there is shown the present invention, which comprises a system 10, and methodology for nonivasive wrinkle removal for the modification of collagen beneath the epidermis. The laser system 10 of the present invention, in a preferred embodiment, utilizes a pulsed dye laser 12 having a deep tissue-penetrating wavelength of about 585 nanometers (nm) laser, so as to target hemoglobin "H" of blood in the skin tissue "T". The preferred pulsed dye laser 12 generates a particular laser wavelength energy of 585 nanometers, which is absorbed by the hemoglobin "H". The heat is generated in the skin tissue "T" area up to about 1 mm in depth and typically uses energy of less than 5 Joules per square cm, having a preferred target spot size "S" of about 10 mm diameter circle or larger.

The pulsed dye laser apparatus 12 of the present invention includes a handpiece 14 connected by an optical fiber or wave guide 16, critically, to a pulsed dye laser generator for generating the particular wavelength and fluence of the present invention.

The handpiece 14 focuses, through a plurality of lenses [20] *22* and [22] *24*, the pulsed dye laser light "L" from the pulsed dye laser generator 12, onto the spot "S" of about 10 mm in diameter or larger, so as to stimulate new collagen growth beneath the epidermis "E".

In the preferred embodiment of the present invention, the pulse width has a range of 150 microseconds to about 1500 microseconds with a preferred width of about 450 microseconds. The wavelength of the pulsed dye laser apparatus 12 of the present invention lies in a range of about 570 nanometers to about 650 nanometers, with a preferred wavelength of about 585 nanometers. The present invention provides a preferred fluence of less than 5 Joules per square cm., and preferably 3 Joules per square cm at a 10-millimeter diameter skin treatment spot "S".

By treating the skin "T" to this low fluence pulsed dye laser light "L", collagen beneath the epidermis, that is below about 0.06 mm. beneath the surface may be stimulated to regenerate and "fill in" valleys of wrinkles for a younger more clearer skin.

Thus what has been shown is a new method of stimulating modification of the collagen layer at a depth of up to about 1 mm to about 1.2 mm beneath the skin surface, utilizing a low energy level of less than 5 Joules per square cm., in a manner not appreciated by the prior art.

What is claimed is:

1. A method for the treatment of wrinkles on human skin, by stimulating collagen growth beneath the epidermis layer, comprising the steps of:

arranging a pulsed dye laser generator in light communication with a pulsed dye laser delivery device;

applying said pulsed dye laser delivery device against tissue having wrinkles;

generating a pulsed dye laser light by said pulsed dye laser; and directing said pulsed dye laser light from said pulsed dye laser delivery device onto said tissue, to reach hemoglobin in a collagen layer beneath the surface of said tissue;

adjusting said range of pulsed dye laser light generated to a wavelength of about 585 nanometers;

generating said pulsed dye laser at a pulse width of about 450 microseconds;

directing said pulsed dye laser light at the tissue at a target spot diameter of about 10-mm; and maintaining a fluence of said pulsed dye laser light of less than 5 Joules per square cm.

2. A method for the treatment of wrinkles on human skin, by stimulating collagen growth beneath the epidermis layer, comprising the steps of:

arranging a pulsed dye laser generator in light communication with a pulsed dye laser delivery device;

applying said pulsed dye laser delivery device against tissue having wrinkles;

generating a pulsed dye laser light by said pulsed dye laser; and directing said pulsed dye laser light from said pulsed dye laser delivery device onto said tissue, to reach hemoglobin in a collagen layer beneath the surface of said tissue; and tuning said pulsed dye laser to deliver a laser light at a wavelength having a range of about 585 nanometers;

generating said pulsed dye laser at a pulse width of about 450 microseconds; and energizing said collagen down to a depth of about 1.0-mm to about 1.2 mm. below the surface of the skin by said pulsed dye laser.

*3. A method for the treatment of wrinkles on human skin, by stimulating collagen growth beneath the epidermis layer, comprising the steps of:*

*arranging a pulsed dye laser generator in light communication with a pulsed dye laser delivery device;*

*applying the pulsed dye laser delivery device against tissue having wrinkles;*

*generating a laser light pulse with the pulsed dye laser generator, the laser light pulse having a wavelength in a range of about 570 nanometers to about 650 nanometers, a pulse width in a range of 150 microseconds to about 1500 microseconds, and a fluence of less than about 5 Joules per cm$^2$; and*

*directing the laser light pulse from the pulsed dye laser delivery device onto the tissue, to reach hemoglobin in a collagen layer beneath the surface of the tissue.*

*4. The method of claim 3, wherein the laser light pulse energizes the collagen down to a depth of about 1.0 mm to about 1.2 mm below the surface of the skin.*

*5. The method of claim 3, wherein the pulsed dye laser delivery device comprises a handpiece connected by an optical fiber or waveguide to the pulse dye laser generator.*

*6. The method of claim 3, wherein the laser light pulse has a wavelength of about 585 nanometers.*

*7. The method of claim 3, wherein the laser light pulse has a pulse duration of about 450 microseconds.*

*8. The method of claim 3, wherein the laser light pulse has a fluence of about 3 Joules per cm$^2$.*

* * * * *